United States Patent
Bauer et al.

(10) Patent No.: US 11,751,996 B2
(45) Date of Patent: *Sep. 12, 2023

(54) SLEEVE AUGMENT DEVICE FOR AN ARTICULATED JOINT

(71) Applicant: WALDEMAR LINK GMBH & CO. KG, Hamburg (DE)

(72) Inventors: Eckhard Bauer, Kiel (DE); Helmut D. Link, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/663,414

(22) Filed: May 13, 2022

(65) Prior Publication Data

US 2022/0273441 A1    Sep. 1, 2022

Related U.S. Application Data

(63) Continuation of application No. 15/742,683, filed as application No. PCT/EP2016/064720 on Jun. 24, 2016, now Pat. No. 11,357,631.

(30) Foreign Application Priority Data

Jul. 9, 2015  (EP) .................................... 15176121

(51) Int. Cl.
*A61F 2/30* (2006.01)
*A61F 2/38* (2006.01)

(52) U.S. Cl.
CPC ...... *A61F 2/30734* (2013.01); *A61F 2/30767* (2013.01); *A61F 2/389* (2013.01);
(Continued)

(58) Field of Classification Search
CPC .. A61F 2002/30545; A61F 2002/30738; A61F 2/30739
See application file for complete search history.

(56) References Cited

U.S. PATENT DOCUMENTS

| | | | |
|---|---|---|---|
| 4,519,101 A | 5/1985 | Schreiber et al. | |
| 4,846,839 A | 7/1989 | Noiles | |

(Continued)

FOREIGN PATENT DOCUMENTS

| | | | |
|---|---|---|---|
| CN | 101172061 A | 5/2008 | |
| CN | 103764180 A | 4/2014 | |

(Continued)

OTHER PUBLICATIONS

Communication Pursuant to Article 94(3) EPC dated Jun. 3, 2022, in connection with European Patent Application No. 16731922.7, 7 pgs.

(Continued)

*Primary Examiner* — Megan Y Wolf
(74) *Attorney, Agent, or Firm* — CHIESA SHAHINIAN & GIANTOMASI PC

(57) ABSTRACT

An augment device for a joint endoprosthesis, the device including a sleeve surrounding a channel extending through the sleeve. The sleeve is formed of porous material for ingrowth of bony material, the sleeve comprising an inner face and an outer face. The sleeve further comprises a wall surrounding the channel, the wall being made of solid material and forming a sandwich structure with the porous material, wherein the wall forms a bulkhead between the inner face and the outer face. Thereby, the bulkhead wall will stop inflow of any cement across the sleeve from its inner to its outer face. The porous material on the outer face will be kept free from cement and its capability to promote bone ingrowth is reliably preserved. The augment devices are preferably provided as a set having different sizes and (Continued)

straight or stepped bottoms for improved versatility and maximum preservation of natural bone matter.

20 Claims, 4 Drawing Sheets

(52) U.S. Cl.
CPC ............... *A61F 2002/30011* (2013.01); *A61F 2002/3092* (2013.01); *A61F 2002/30148* (2013.01); *A61F 2002/30449* (2013.01); *A61F 2002/30471* (2013.01); *A61F 2002/30545* (2013.01); *A61F 2002/30571* (2013.01); *A61F 2002/30616* (2013.01); *A61F 2002/30736* (2013.01); *A61F 2002/30738* (2013.01); *A61F 2002/30772* (2013.01); *A61F 2002/30805* (2013.01); *A61F 2002/30827* (2013.01)

(56) References Cited

U.S. PATENT DOCUMENTS

| | | | |
|---|---|---|---|
| 4,961,748 | A | 10/1990 | Frey et al. |
| 5,108,432 | A | 4/1992 | Gustavson |
| 11,357,631 | B2 * | 6/2022 | Bauer ................ A61F 2/30767 |
| 11,406,501 | B2 * | 8/2022 | Bauer ................ A61F 2/30734 |
| 2003/0033019 | A1 | 2/2003 | Lob |
| 2003/0065397 | A1 | 4/2003 | Hanssen et al. |
| 2004/0162619 | A1 | 8/2004 | Blaylock et al. |
| 2005/0107883 | A1 | 5/2005 | Goodfried et al. |
| 2008/0262626 | A1 | 10/2008 | Raugel |
| 2009/0171389 | A1 * | 7/2009 | Sankaran ............... A61F 2/4611 623/17.11 |
| 2010/0114323 | A1 | 5/2010 | Deruntz et al. |
| 2011/0009974 | A1 | 1/2011 | Blaylock et al. |
| 2011/0202141 | A1 | 8/2011 | Metzger et al. |
| 2012/0016485 | A1 | 1/2012 | Sharp |
| 2012/0089227 | A1 | 4/2012 | Jarzem |
| 2013/0172892 | A1 | 7/2013 | Servidio et al. |
| 2014/0081410 | A1 | 3/2014 | Lieberman et al. |
| 2014/0099353 | A1 | 4/2014 | Link |

FOREIGN PATENT DOCUMENTS

| | | |
|---|---|---|
| EP | 0281984 A1 | 9/1988 |
| EP | 2130516 A1 | 12/2009 |
| WO | 2013/102089 A1 | 7/2013 |
| WO | 2015/145348 A1 | 10/2015 |

OTHER PUBLICATIONS

Office Action dated Apr. 7, 2020, in connection with Japanese Patent Application No. 2018-500480 and its English translation.
Translation of EP0281984A1 retrieved from espacenet on May 8, 2020 (Year: 2020).
Office Action dated Jan. 24, 2019 in connection with Chinese Patent Application No. 201680040561.1.
International Search Report and Written Opinion dated Sep. 1, 2016, in connection with International Patent Application No. PCT/EP2016/064720, 11 pgs.

* cited by examiner

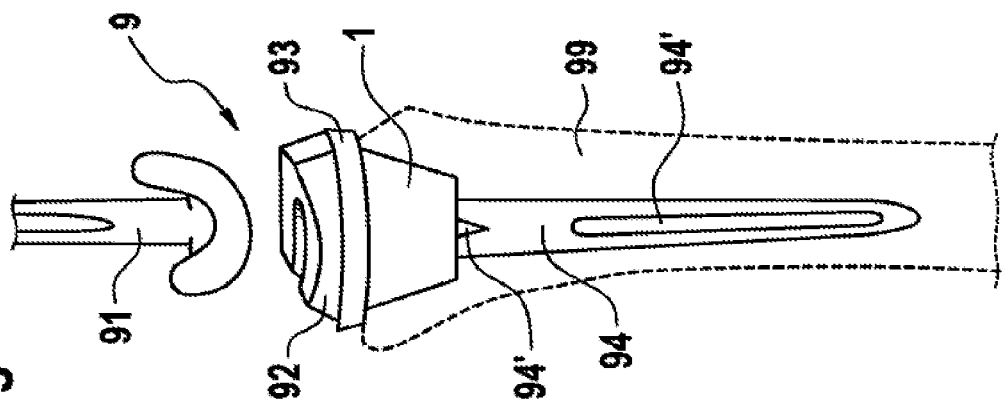
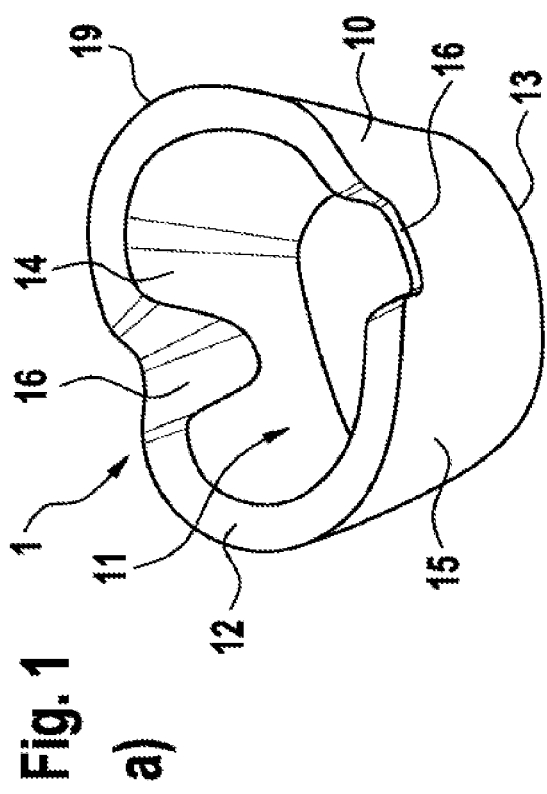
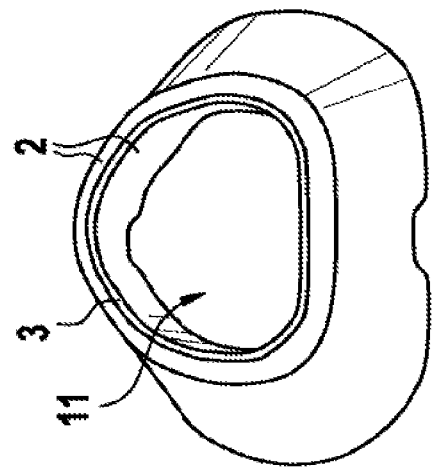

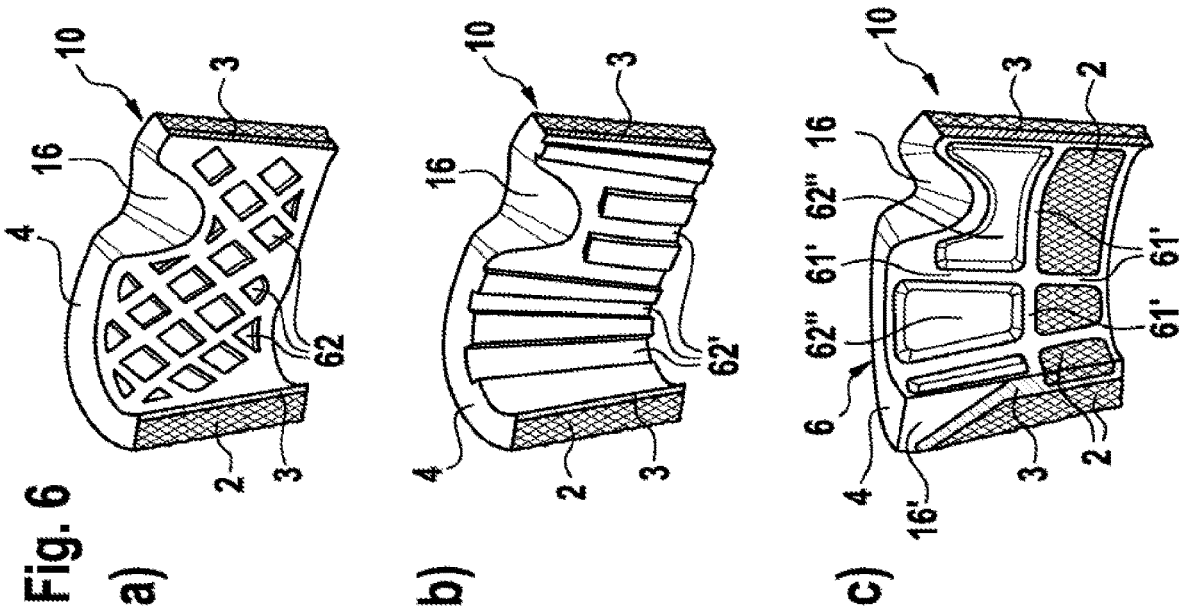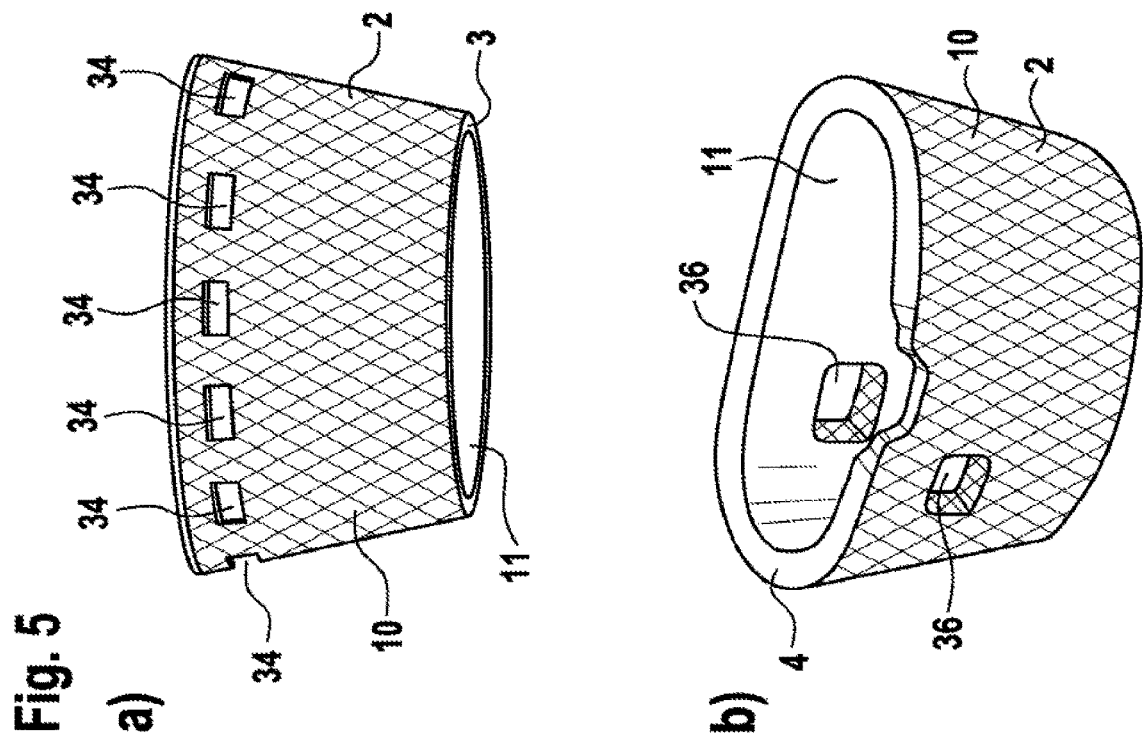

SLEEVE AUGMENT DEVICE FOR AN ARTICULATED JOINT

The invention relates to an augment device for a joint endoprosthesis. The mentioned particularly refers to a tibial augment for a knee joint endoprosthesis.

Due to diseases, injuries or wear, particularly due to high age, replacement of joints in a body, such as knee, shoulder, elbow, with endoprothetic implants is common. Due to other illness or due to an explanting of a failed endoprosthesis it is not uncommon to find an implantation side for the endoprosthesis which is pathologic, mainly due to bone defects in its vicinity. This is a problem for the surgeons since a lack of strong bone near the joint implantation side could render implantation of the endoprosthesis impossible or could lead to premature failure. Since such bone defects are encountered quite often, various approaches to remedy the situation have been devised.

In particular for such indications, wherein a joint endoprosthesis is to be used, it is known to provide an augmentation device which is configured to fill a gap left by defective bone. Such an augmentation device having the form of a sleeve is e.g. disclosed in U.S. Pat. No. 8,506,645 B2. Accordingly, defective bone material will be removed and the cavity created thereby will be filled by placing of the augment device. The shape of sleeve serves a purpose of allowing the stem of a stemmed endoprosthesis to pass through its central opening, which forms a channel for the stem. The sleeve itself is configured to be impacted into the cavity.

It comprises a body formed with porous metal material for facilitating bony ingrowth. However, preparing the site for reception of the augment device in a precise manner is difficult. Whereas cement may be used to fill any gaps that may exist or to provide better seating for the augment device in general, there is a problem that the cement enters the porous metal material, thereby rendering the desired ingrowth promoting characteristic rather useless. Further, such entering of cement would make difficult any future removal of the augment device.

It is also an object of the invention to provide an improved augment device that lessens this draw back.

The solution according to the invention resides in the features of the independent claims. Preferable embodiments are the subject matter of the dependent claims.

An augment device for a joint endoprosthesis, in particular a tibial augment for a knee joint endoprosthesis, comprising a sleeve surrounding a channel extending through the sleeve from a top to a bottom of the sleeve, the sleeve being formed of porous material which is configured for ingrowth of bony material, the sleeve comprising an inner face and an outer face, the inner face defining the channel and a distance between the inner face and the outer face defining a thickness is according to the invention configured such that the sleeve further comprises a wall surrounding the channel, the wall being made of solid material and forming a sandwich structure with the porous material, wherein the wall forms a bulkhead between the inner face and the outer face, the bulkhead being configured for blocking cement flow between the inner face and the outer face.

It is the gist of the invention to provide a sandwich structure for the sleeve, the sandwich structure being a compound of a solid wall and the porous material. By virtue of this, the solid wall will act as a bulkhead stopping inflow of cement across the thickness of the porous material. The cement may flow only so far until it reaches the bulkhead, and it will be stopped there. Thereby it is avoided that the outer porous structure is virtually filled with cement used in the channel, thereby preserving the bone ingrowth promoting effect of the porous material being kept free from cement. As a further advantage, the solid wall serves as a reinforcing element which provides greater stiffness to the sleeve. The solid wall thus serves two purposes, namely first that of being a bulkhead protecting a portion of the porous material against inflow of cement thereby preserving the desired bone ingrowth capability of said porous material and further by providing a greater stiffness. These two advantages are intertwined with each other, particularly since the wall provides some reinforcement allowing a higher degree of porosity for even more improved bone ingrowth capability, without compromising mechanical stability. There is no precedent for such a unique, advantageous combination.

The wall may be positioned at the inner face. Thereby, the porous material will be completely placed on the outside, providing full bone ingrowth capability to the surrounding bony material. Optionally, porous material will be placed on the interior side, too. Alternatively, a raised structure having embossments may be placed on the inner face of the wall, thereby providing an improved bonding surface for cement applied within the channel and facilitating removal as opposed to the variant having porous material on the inner face.

The porous material is preferably of a high porosity (e.g. total porous volume at least 60%-90% of total volume) and comprises interconnected pores. Owing to such a high porous structure ingrowth of bony material will be highly facilitated.

Preferably, the wall extends along an entire height from the bottom of the top to the sleeve. Thereby it forms a complete bulkhead reaching over the entire device, shielding the complete inner space from any cement influx from the outside. This can be further improved by providing a top cover made of solid material which is configured such that it covers essentially the complete top of the sleeve. The augment device is thereby also protected against influx of cement from above. It is further preferred to form the top cover and the wall as a unitary element. Thereby a complete bulkhead is formed, protecting against influx from the outer face as well as from a top.

Preferably, the augment device features a conical form such that its total width is tapering down towards its bottom end. It is preferably configured such to be wider at its top and to have a cone angle between 10° and 45° (measured as an imaginary apex angle). However, the conic form does not need to be perfect. In fact, it is preferable that the sleeve comprises at least one interior recess. Such an interior recess provides additional space for accommodating a stem of the endoprosthesis, including any ribs that may be located on the stem or any other projection which may be present on the outer circumference of the endoprosthesis which otherwise could come in conflict with the inner face and/or top cover of the sleeve. In order to maintain full bulkhead functionality, a top cover preferably comprises further at least one extension cover which is configured to cover side faces and/or a bottom face of the interior recess. Further preferably, the top cover and the extension covers are connected such as to provide a continuous top bulkhead. Optionally, the top cover, extensions and the porous material may be formed as an unitary element. Thereby, even in the case of providing such recesses the full bulkhead functionality of the wall and the top cover will be preserved.

Preferably the edges of the sleeves are at least partly rounded and/or bevelled. Thereby it blends more easily into its cavity of the bone to which it is to be implanted. Further, it provides less of a cutting hazard for the surgeon in handling the augment device.

Preferably a raised structure having embossments is formed on the inner face. Thereby, the inner face will become nonsmooth, thereby providing greater friction between any cement applied in the channel and the wall. Due to the depressed nature of the embossments a light interlocking effect may be achieved, however this effect will be small enough to be easily overcome in case a removal of the augment device shall be performed. Preferably, the embossments are groovings which are preferably oriented in a direction pointing from the bottom to a top of the sleeve. By virtue of this, the cement applied in the channel blocks any unwanted sideways movement relative between the cement and the augment device. However, owing to the orientation of the groovings running from the bottom to the top any removal is facilitated, since such a removal would be done by moving the augment device in said direction. This effect can be even more pronounced if the groovings are configured such as to be tapering in width. However, other configurations could be chosen for the raised structure with its embossments. Another preferred embodiment is having the embossments arranged in a matrix like fashion, wherein the individual embossments are preferably configured to have a checkered or diamond structure. Alternatively or additionally, a lattice structure is provided, the lattice structure comprising laths and interspaces. Interspaces are configured such as to be filled by the porous material, whereas the laths provide additional structure reinforcement and thereby achieve an improved bonding of the porous material to the wall. The laths may be separate elements, but it is preferred that they are formed unitary with the wall.

In a particularly preferred embodiment, which may be the subject of independent protection, the sleeve comprises at least one bending joint, the bending joint being configured for compressing the channel. Further preferably, two or more bending joints are arranged in a mirror symmetric fashion. Due to the bending joints the sleeve may be compressed from the outside and will achieve a decreased circumference and width, enabling it to be put into a tight cavity of the bone more easily. Since the cavity is often dimensioned to be rather tight for improved mechanical stability of the augment device and the endoprosthesis in the bone, and further to preserve as much of healthy bone as possible, there is a problem that forcing the augment device into a tight cavity may create a risk of creating cracks in the bone. By virtue of the bending joints, rather than cracking the bone the sleeve itself will compress itself to a smaller size, thereby allowing it to be more easily placed into the cavity without the risk of cracking surrounding bone material. In a preferred embodiment, the bending joint is formed by a void in the sleeve, wherein a strip of solid material spans the void. Preferably, the strip is oriented such as to be oblique with respect to the wall, further preferably such that a lower end of the strip is positioned closer toward the outer face than an upper end of the strip which is positioned closer toward the inner face. The strip acts as a hinge providing the degree of movement required for bending a part of the sleeve in respect to the other part. Further, an axis of the hinge as formed by the strip is defined by the orientation of the strip. Rather than orienting the strip to parallel to a middle chord of the wall, it is oriented oblique to it. Thereby the bending access will not be parallel to the plane of the wall, instead it will be parallel or at least nearly parallel to a center axis of the channel. The degree of oblique orientation is defined by the cone angle of the sleeve. In other words, the oblique arrangement of the strip counteracts the effect of the conically formed wall and ensures a compressing in a horizontal plane parallel to the top cover.

In a further preferred embodiment, the strip is configured to have a reduced bending stiffness in a lower portion, preferably by means of a tapering width. Owing to the lower bending stiffness the contribution of the lower portion to the overall bending stiffness is rather small. As a result, the percentage reduction of the stiffness of a shorter bending joint is smaller than the percentage reduction of the length of that bending joint where all bending joints—although having different lengths—end at the top of the sleeve, e.g. at a sleeve having a stepped bottom.

Further preferably, the sleeve comprises a compensator element configured for adjusting a circumference of the sleeve in a bended state of the bending joint. The compensator element allows a degree of freedom for absorbing a reduction of the circumference which will be realized by moving the bending joints under compressive force. Preferably, the compensator element is configured as at least two overlapping tongues being in sliding relationship. Owing to the sliding relationship, the tongues maintain the bulkhead functionality even in the area of the compensator element. Further, the sliding relationship allows a variance in length and thereby the reduction of the circumference.

In a preferred embodiment a plurality of small holes are provided in the wall. The term "small holes" is to be construed such that the holes have a diameter being so small that it blocks cement from passing through said holes. Thereby the bulkhead functionality in respect to cement is preserved. However, the presence of the small holes further improves bone ingrowth and, more importantly, serve as aeration holes venting pockets of trapped air which may otherwise be formed between the inner surface of the wall and inflowing cement. By virtue of the small holes air can escape more easily thereby implantation with cement is facilitated and made more reliable.

Further, windows may be provided in the wall, preferably arranged in a row close to the top. Further preferably, the windows are extending through the porous material, too. The windows form deliberate openings for the cement, such that the cement place on an internal side may pass through the windows towards the outer side in a controlled manner. Thereby unwanted distribution of cement is kept controlled. By allowing the cement to flow through the windows results in the cement forming pin-like projections reaching through the windows, thereby arresting the position of the augment device like fixation pins. This provides for an improved fixation. Further, by positioning the windows close to the top these fixation pins may be easily cut in case of a removal of the augmentation device. Additionally or as an alternative, a large passageway is provided in the wall and the porous material, thereby extending through entire sleeve. The passageway is orientated perpendicular to the channel. Preferably, the passageway is positioned in a middle portion of the wall. Further preferably, the passageway features rounded corners for improved resistance against cracking. By virtue of the passageway, a rather large fixation trunnion is formed by allowing cement flow through it in a controlled manner, and providing a very solid fixation trunnion. The term "large" is to be construed such as to mean a cross-section area that is at least three times the area of a single window.

In many cases the augment device will have a flat bottom surface. However, preferably embodiments are provided which are having a stepped bottom surface having two sections, one section in which the augment device has its full height and another section where it has a reduced height. Preferably the bottom is stepped such that the height in the reduced portion is about 0.4 to 0.7 of the full height. Further preferably, a transition between the section with full height and the section with reduced height is in the middle of the sleeve along a line of the symmetry, dividing the sleeve in a left and a right part. However, that transition may be offset to either side if so desired.

According to a further embodiment of the invention, which may be the subject of independent protection, a set of augment devices as defined above are provided, wherein the set comprises a first type of augment devices having a full height and a second type of augment devices having a reduced height, wherein the reduces height is preferably 0.4 to 0.7 of the full height.

Further preferably, the set comprises a third type which has a stepped bottom surfaces. Further preferably, the set comprises the said types in different sizes, preferably ranging from small over medium to large.

In the following the invention will be described according to the accompanying drawing in an exemplary manner. In the drawings:

FIG. 1 *a, b* is a perspective view of a first exemplary embodiment;

FIG. 2 is a schematic view showing an augment device according to the invention in situ;

Figure 7:
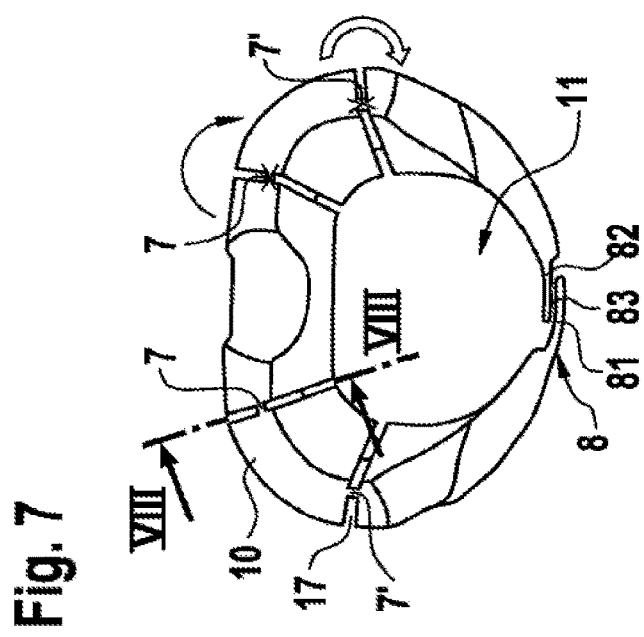
Figure 8:
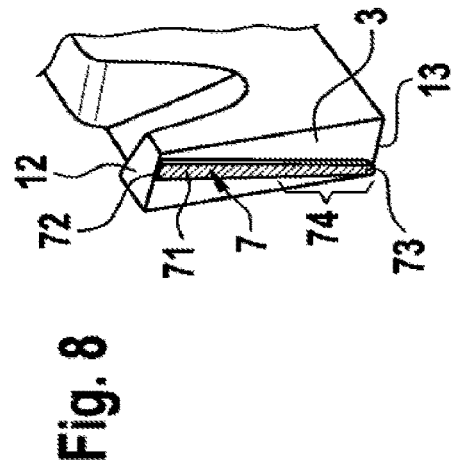

FIG. 5 *a, b* are perspective views of a second and third embodiment having windows and a passageway, respectively;

FIG. 6 *a-c* are detail views showing a raised structure on an inner face;

FIG. 7 is a top view of a fourth embodiment having bending joints;

FIG. 8 is a detailed cross section trough one of the bending joints; and

Figure 9:
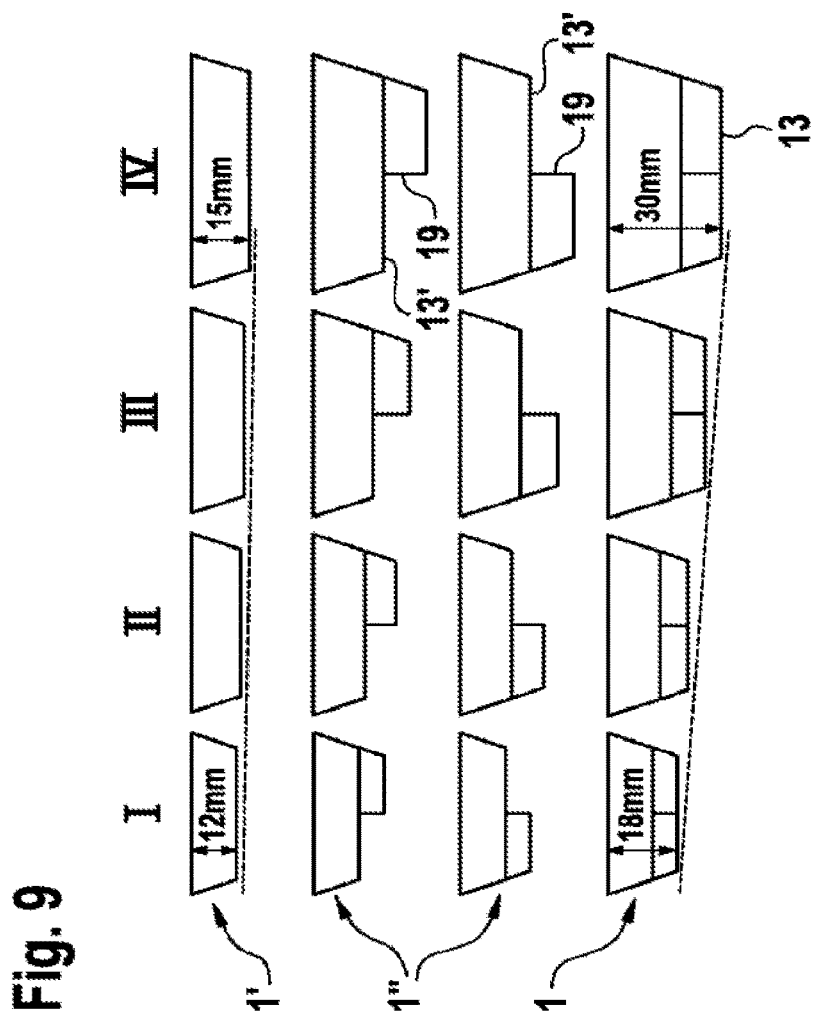

FIG. 9 shows a set of augment devices of different types.

A first embodiment of an augment device 1 according to the present invention is shown referring to FIGS. 1-4. The augment device 1 of this embodiment is preferably a tibial augment which is made of a biocompatible metallic material. It is preferably selected from a group comprising titanium alloys, pure titanium, cobalt chromium, stainless steel, tantalum and zirconium. Further preferably, the material is pure titanium (for example Ti Grade 2). This combines excellent biocompatibility with good strength and stiffness characteristics. Another preferred material is a titanium alloy (for example Ti6Al4V). This material is more regularly available, also it has a higher stiffness.

The tibial augment has a generally conic form of a sleeve 10. The sleeve 10 surrounds a channel 11 which runs entirely through the augment device 1 from its top 12 to its bottom 13. The channel 11 is configured for receiving a stem of an endoprosthesis, in particular the stem 94 of a tibial part 92 of a knee prosthesis 9.

The sleeve 10 is made in a sandwich configuration having a wall 3 combined with two layers of porous metal material 2. It is to be noted that the porous portion at the inner face is optional; alternative configurations are shown in FIG. 6*a, b, c*. The wall 3 runs from the bottom 13 to the top 12 of the sleeve 10 surrounding completely the channel 11. On the top 12 the wall 3 meets a top cover 4 which covers a complete top side 12 of the sleeve 10. The top cover 4 and the wall 3 form a unitary piece. Thereby, the wall 3 in conjunction with the top cover 4 act as a bulkhead blocking any passage of cement from the channel 11 to an external side of the sleeve 10.

The tibial augment 1 is configured such as to be anatomically sized and shaped to fill a cavity in an upper part of a distal bone 99, namely the tibia. The augment device 1 is formed generally conically for better fitment. Its bottom side 13 is generally planar as well as its top 12.

Figure 3:
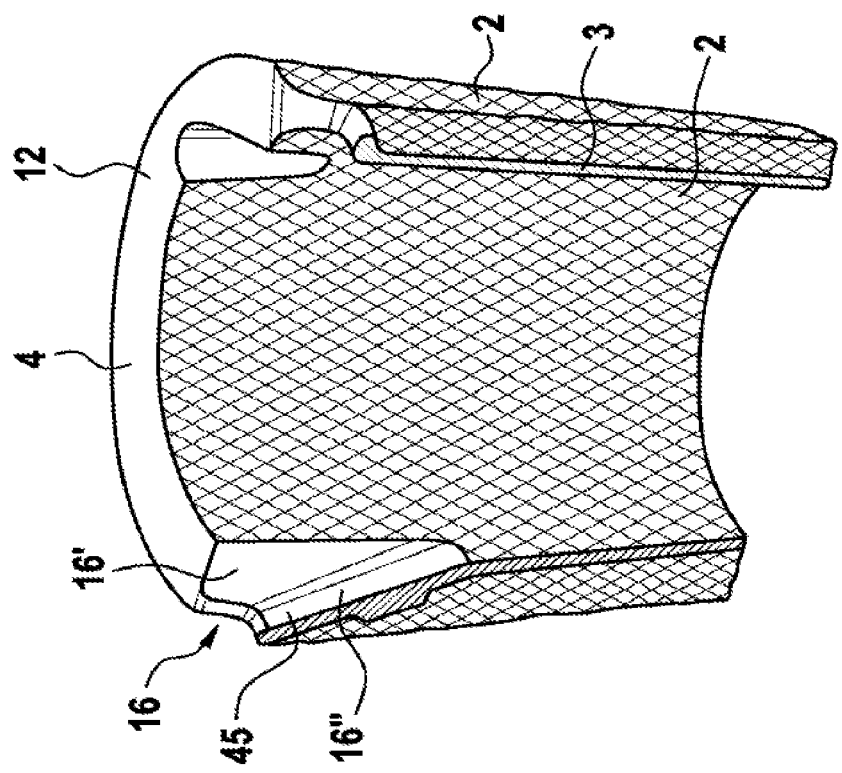
FIG. 3 is a cross section of the embodiment depicted in FIG. 1.

As it can be appreciated in FIG. 2, the augment 1 is placed in the cavity of an upper portion of the bone 99, thereby forming a base on which a tibial plate 93 of the tibial component 92 of the knee prosthesis 9 is to be positioned. The knee prosthesis 9 further comprises a femur component 91 configured for rotatable interaction with the tibial portion 92. The tibial component 92 further comprises a stem 94 configured to be anchored in a medullary channel of the tibia 99. The stem 94 is routed through the channel 11 of the tibial augment 1. In order to provide sufficient room for any ribs 94', or other projections on the stem 94 or the tibial part 92 generally, the tibial augment 1 is further provided with recesses 16 in order to provide additional room for the stem 94 and its projections 94'. The recesses 16 may be configured like depressions as depicted in FIG. 3, having a bottom face 16" and side face 16'. In order to provide a continuous top bulkhead, the bottom face 16" and the side face 16' is closed by an extension cover 45 which functions as an extension of the top cover 4. Thereby, a continuous bulkhead on the top side is achieved, thereby avoiding any unwanted leakage of cement trough the recesses 16.

A porous material 2 placed on the outer face of the wall 3 is preferably a highly porous material having a degree porosity of at least 60-90%. Further, the pores are interconnected and elementary cells defining the pores are arranged in a regular order. The interconnected pores provide for a much improved ingrowth of bony material, and thereby ensure a good stabilization of the tibial augment 1 in the tibial bone 99.

Examples for alternative embodiments of the inner face are shown in FIG. 6*a-c*. FIGS. 6*a* and 6*b* show the inner face without and FIG. 6*c* with a porous portion on the inner face, however it is to be noted that the porous portion is entirely optional and either embodiment may be provided with or without it. In these embodiments the inner face is provided with a raised structure 61 having embossments 62 there between. In a first variant shown in FIG. 6*a*, the embossments 62 are configured to have a diamond shape and to be arranged in a matrix like fashion. This provides for additional fixation in both, horizontal as well as vertical direction. In FIG. 6*b* a variant is shown having the embossments configured as groovings 62', the groovings 62' being oriented to run in a direction form the bottom to the top of the sleeve 10. This provides for an improved fixation effect in respect to a horizontal direction, but allows for a facilitated removal of the augment device in a vertical direction. In FIG. 6*c* a variant is shown having a lattice structure 6 provided on the inner face. The lattice 6 comprises laths as raised structure 61 and interspaces 62" as embossments. The laths 61 define a grid, with the interspaces 62" being arranged there between. The interspaces 62" are configured to be optionally filled by the porous material 2, preferably such that it will be flush with the surface of the laths 61 in a filled state. The lattice structure 6 enhances fixation and has a considerable reinforcing effect on the sleeve 10, thereby providing addition mechanical strength.

For implantation cement may be applied for fixation of the stem 94. For this reason, the cement will be applied within the channel 11 around the stem 94. The cement may flow into the porous material 2 placed on an inner face of the wall 3, thereby providing a strong, interlocked bonding. However, in order to preserve the positive bone ingrowth effect of the porous material 2, the cement shall not reach the outer face. For this purpose the wall 3 is provided acting as a bulkhead confining the cement to an inner portion, thereby keeping the outer face essentially cement-free. The top cover 4 ensures that no cement could spill over towards the top. A bottom cover is not necessary. However, it may be provided at the section of the bottom outward of and including the wall, thereby blocking any unwanted influx of cement in the porous material 2 on the outer face.

Figure 4:
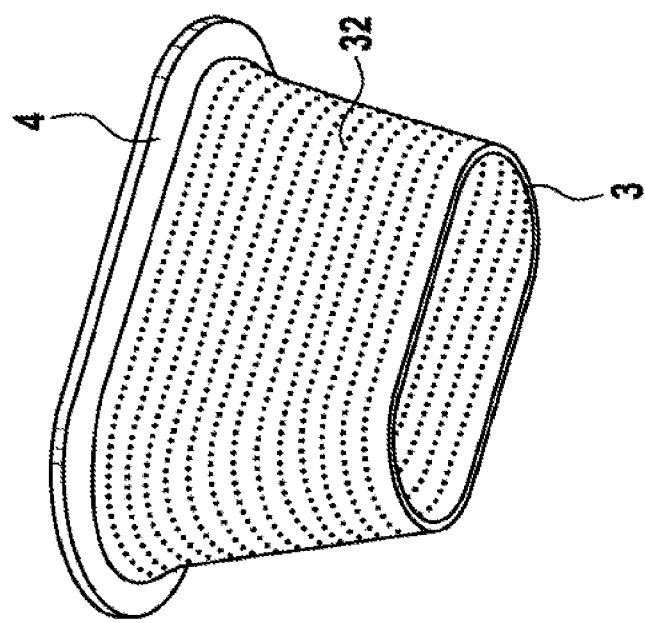
FIG. 4 is a detailed view of a wall of the augment device.

In order to allow a smooth influx of the cement into porous material 2 on the inner face it is necessary to remove air displaced by the cement from the inner portion. In order to facilitate removal of air in order to avoid the air being trapped, a plurality of small holes 32 are provided in a regularly arranged manner at the wall 3, preferably at the entire wall 3. This is depicted in FIG. 4. The size of the holes 32 is dimensioned such as to allow passage of gases like air, but has to block any passage of a cement. A preferred size is between 0.3 to 0.5 mm.

Now referring to FIG. 5, second and third embodiments are shown being provided with additional means for fixation. To this end, windows 34 are provided in a row close to a top end of the sleeve 10. The windows 34 configured such as to penetrate the wall 3 and preferably the porous material 2 on either side. Upon implantation and application of cement, the cement flows freely through the windows 34 from the channel 11 outwards to the exterior. Since that flow of cement is confined to the vicinity of the windows 34 no adverse effect are encountered with respect to promoting bone ingrowth capability of the porous material 2 on the outer face. Yet, the cement flowing through the windows 34 acts like additional fixation pins securing the tibial implant 1 into its place. This allows for a better and considerable faster fixation of the augmentation device 1. A further advantage of this configuration is, that in a case of a required removal of the augment device 1 the cement pins reaching through the windows 34 could be easily cut from the outside owing to the proximity of the windows 34 to the top 12 of the sleeve 10. Thereby any removal will be facilitated by maintaining the high degree of stabilization during implantation.

Additionally or alternatively, as depicted in figure in 5b a rather large passageway 36 can be formed in a more central area of the sleeve 10. The passageway 36 runs through the wall 3 and the porous material 2. The passageway 36 is oriented essentially perpendicular to a center axis of the channel 11. The dimension of the passageway 36 through the wall 2a is selected such that it has more than three times the area of any of the windows 34. Thereby, by flowing of cements trough the passageway 36 a rather massive trunnion for additional fixation strengths will be formed. Similarly as explained above in respect to the windows 34, this additional fixation could be rather easily removed in case of a removal by cutting of the cement trunnion. In the depicted exemplary embodiment the passageway is dimensioned to be 10×8 mm.

A further embodiment is shown in FIGS. 7 and 8. This embodiment features two sets of bending joints 7, 7'. The bending joints allow a bending of the sleeve 10 such that it will be compressed as a whole, thereby reducing the size of the channel 11 and the outer dimension of the sleeve 10. The bending joints 7, 7' is formed by a void 17 in the sleeve 10 combined with a metal strip 71 which spans the void 17. As best appreciated in FIG. 8, the metal strip 71 is of solid material and runs from a top 12 to a bottom 13 of the sleeve 10. The strip 71 is oriented oblique with respect to the wall 3 such that a lower end 73 of the strip 71 is positioned closer toward the outer face of the wall 3 and the upper end 72 of the strip 71 is placed closer to the inner face of the wall 3. By virtue of this arrangement, the strip 71 is oriented essentially parallel to a center axis of the channel 11. Thickness of the strip 71 at a lower portion 74 is reduced. To this end, the strip 71 is configured such as to have a tapering width towards its lower end 73. By virtue of this tapering, the most bending force will be created by the upper part of the strip 71, whereas the lower portion 74 will only contribute to the bending force to a much lesser degree.

The bending force and movement effected thereby is depicted with respect to FIG. 7. Two pairs of bending joint 7, 7' are provided in a mirror symmetric configuration. A first set of bending joints 7 is placed at a rear wall of the sleeve 10. By exerting a bending force, the bending joints 7 allow for a movement in a rotational direction as indicated by the single arrow. Thereby an axis of bending defined by the bending joints 7 provides for an elasticity in a medio-lateral (ML) direction.

A second set 7' is provided which is arranged in a mirror symmetric configuration at the side portion of the sleeve 10. The bending joints 7' provide a range of motion as depicted by the double arrow. This provides for an axis of bending which gives anterior/posterior (AP) elasticity. As a result, by providing both pairs of bending joints 7, 7' compressibility in two dimensions is achieved, namely one in ML direction and another in AP direction.

By exerting bending force the width of the inner channel will be reduced. Thereby, its circumference will be reduced. In order to enable the sleeve 10 for such a reduction, a compensator element 8 is provided. In the depicted embodiment (see FIG. 7) it is arranged at an opposite, front side of the sleeve 10 to the bending joints 7. The compensator element is comprised of two tongues 81, 82 arranged at a left and a right portion of the sleeve 10. The tongues 81, 82 are arranged in an overlapping configuration, leaving just a tiny gap 83 there between. The tongues 81, 82 slide along each other under the effect of a bending motion with the bending joints 7, 7'. The gap 83 is dimensioned such as to small enough to block leakage of cement.

The bottom 13 of the augment device 1 may be flat or stepped (see FIG. 9). In the stepped variant, a portion 13' with a reduced height is present on either the left or the right side. A transition surface 19 connects the portion with full height with the portion 13' having a reduced height.

Further, additional types are provided that have a reduced height over the entire area. This type is depicted as type 1' in FIG. 9. The type having the stepped bottom is depicted as type 1" whereas the original type as depicted in FIG. 1-8 is shown as type 1 in FIG. 9.

Preferably, a full set of augment devices is provided. The set comprising the types as mentioned above. Additionally, the types are provided in different sizes I, II, III and IV, with I being extra small, II being small, III being medium; and IV being large. This allows the surgeon a rather broad range of options in order to select an appropriate augment device 1 depending on the actual conditions of the implant site.

The invention claimed is:

1. An augment device for a joint endoprosthesis, the device comprising:
a sleeve having a top and a bottom, a distance between said top and said bottom defining an entire height of said sleeve, wherein the sleeve surrounds a channel extending through the sleeve from the top to the bottom of the sleeve wherein the channel is configured to receive a stem of the joint endoprosthesis,
the sleeve being formed of porous material and comprising an inner face and an outer face, the inner face defining the channel, and a distance between the inner face and the outer face defining a thickness, wherein the porous material is configured for ingrowth of bony material, the sleeve further comprising a wall that surrounds the channel and extends along the entire height of the sleeve, the wall being made of solid material and forming a layered structure with the porous material;

the sleeve further comprising at least one bending joint, said at least one bending joint having a lower bending stiffness in a lower portion than in an upper portion and extending for the entire height.

2. The augment device of claim 1, wherein the sleeve is compressible in at least one of the media-lateral direction and the anterior/posterior direction.

3. The augment device of claim 1, wherein the wall forms a complete bulkhead reaching over the entire device between the inner face and the outer face, the bulkhead being configured for blocking cement flow between the inner face and the outer face.

4. The augment device of claim 1, wherein the wall serves as a reinforcing element.

5. The augment device of claim 1, wherein the wall is located at an intermediate position along a direction of the thickness such that the porous material is formed on an inward facing side and an outward facing side of the wall.

6. The augment device of claim 1, wherein the sleeve is of a generally conical shape.

7. The augment device of claim 6, wherein the sleeve is wider at its top and has a cone angle between 10° and 45°.

8. The augment device of claim 1, wherein the augment device is a tibial augment for a knee joint endoprosthesis.

9. The augment device of claim 1, wherein the porous material comprises interconnected pores.

10. The augment device of claim 1, further comprising a top cover made of solid material, wherein the top cover completely covers a top surface of the sleeve and leaves the channel open.

11. The augment device of claim 10, wherein the sleeve comprises at least one recess and the top cover further comprises at least one extension cover which is configured to cover side faces or a bottom face of the at least one recess.

12. The augment device of claim 11, wherein the top cover and the at least one extension cover are connected such as to provide a continuous top bulkhead.

13. The augment device of claim 1, wherein edges of the sleeve are at least partly rounded, at least partly beveled, or at least partly rounded and beveled.

14. The augment device of claim 1, wherein a raised structure having embossments is formed on the inner face.

15. The augment device of claim 1, wherein a passageway extends through the entire sleeve, said passageway oriented to run across the channel.

16. The augment device of claim 1, wherein the at least one bending joint comprises a void in the sleeve and a metal strip, wherein the metal strip spans the void.

17. The augment device of claim 16, wherein the metal strip is oriented oblique with respect to the wall such that a lower end of the metal strip is positioned closer toward the outer face and an upper end of the metal strip is closer to the inner face.

18. The augment device of claim 16, wherein the metal strip is oriented substantially parallel to a center axis of the channel.

19. The augment device of claim 1, wherein the sleeve comprises a compensator element configured for adjusting a circumference of the sleeve in a bending state of the at least one bending joint.

20. The augment device of claim 19, wherein the compensator element is configured as two overlapping tongues arranged in a sliding relationship.

* * * * *